United States Patent [19]

Kolditz et al.

[11] Patent Number: 4,765,314
[45] Date of Patent: Aug. 23, 1988

[54] DEVICE FOR INTRODUCING AN ENDOSCOPE OR A SURGICAL TOOL INTO BODY CAVITIES WITH A FEED FOR A FLUSHING MEDIUM AND AN EXTRACTOR FOR SAID FLUSHING MEDIUM

[75] Inventors: Dietmar Kolditz, Bochum; Hans Keller, Dürbheim; Karl Ernst-Kienzle, Immendingen, all of Fed. Rep. of Germany

[73] Assignee: Aesculap-Werke Aktiengesellschaft, Tuttlingen, Fed. Rep. of Germany

[21] Appl. No.: 815,584

[22] Filed: Jan. 2, 1986

[30] Foreign Application Priority Data

Jan. 9, 1985 [DE] Fed. Rep. of Germany ....... 3500444

[51] Int. Cl.⁴ .............................................. A61B 1/00
[52] U.S. Cl. ..................................................... 128/4
[58] Field of Search ......................... 128/4–8, 128/303.15, 17, 18, 303.1, 750, 752, 758, 772; 73/151

[56] References Cited

U.S. PATENT DOCUMENTS

| | | | |
|---|---|---|---|
| 2,487,502 | 11/1949 | Willinsky | 128/4 |
| 2,584,619 | 2/1952 | Rubens et al. | 128/5 |
| 2,767,705 | 10/1956 | Moore | 128/4 |
| 3,835,842 | 9/1974 | Iglesias | 128/7 |
| 3,866,601 | 2/1975 | Russell | 128/4 |
| 3,980,078 | 9/1976 | Tominaga | 128/4 |
| 4,132,227 | 1/1979 | Ibe | 128/4 |
| 4,167,944 | 9/1979 | Banks | 128/6 |
| 4,201,199 | 5/1980 | Smith | 128/6 |
| 4,254,762 | 3/1981 | Yoan | 128/4 |
| 4,325,362 | 4/1982 | Ouchi et al. | 128/4 |
| 4,424,833 | 1/1984 | Spector et al. | |

FOREIGN PATENT DOCUMENTS

| | | | |
|---|---|---|---|
| 2449559 | 4/1976 | Fed. Rep. of Germany | |
| 2428000 | 7/1977 | Fed. Rep. of Germany | |
| 2902829 | 8/1979 | Fed. Rep. of Germany | |
| 2850021 | 3/1980 | Fed. Rep. of Germany | |
| 2915271 | 10/1980 | Fed. Rep. of Germany | 128/4 |
| 738956 | 1/1933 | France | |
| 979425 | 4/1951 | France | 128/6 |
| 635143 | 4/1950 | United Kingdom | 128/6 |

Primary Examiner—Max Hindenburg
Attorney, Agent, or Firm—Wolf, Greenfield & Sacks

[57] ABSTRACT

A device for introducing an endoscope or a surgical tool into body cavities with a feed for a flushing medium and an extractor for said flushing medium, which permits as versatile as possible an application of the endoscope or tool and maintains a higher pressure in the interior of the body as compared with the environment. The device includes a sluice, insertable into the body cavity from outside. The sluice has a cylindrical stem along whose inner wall extend two separate longitudinal grooves which have openings at their ends which pass through the wall of the stem. The openings outside the body are connected to the feed and the extractor for the flushing medium. A cylindrical endoscope or tool is inserted into the device with its outer wall tightly contacting the inner wall of the stem. The outer wall of the endoscope or tool, together with the longitudinal grooves of the stem, form sealed channels for the flushing medium.

9 Claims, 1 Drawing Sheet

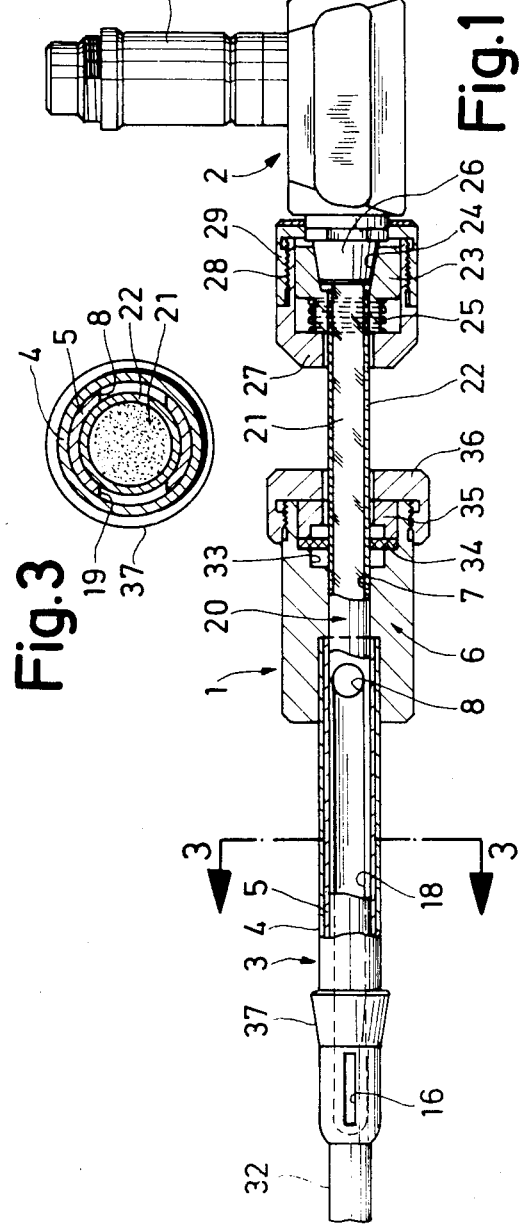
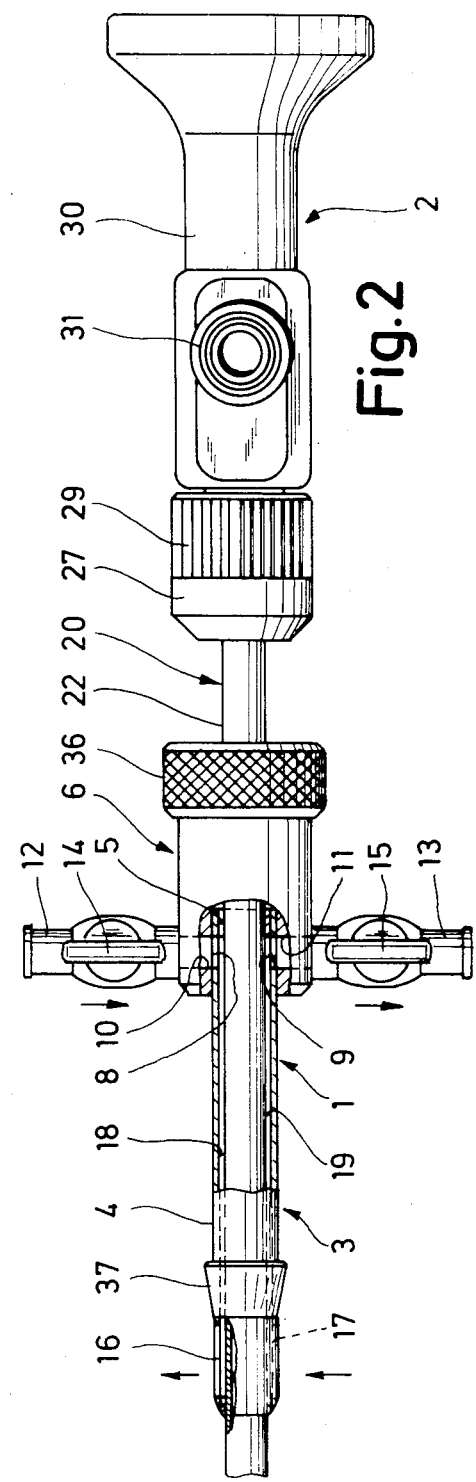

DEVICE FOR INTRODUCING AN ENDOSCOPE OR A SURGICAL TOOL INTO BODY CAVITIES WITH A FEED FOR A FLUSHING MEDIUM AND AN EXTRACTOR FOR SAID FLUSHING MEDIUM

The invention relates to a device for introducing an endoscope or a surgical tool into body cavities with a feed for a flushing medium and an extractor for said flushing medium, and more particularly to such a device which maintains an overpressure in the interior of the body.

In body cavities, for example in the knee joint, in order to be able to diagnose or operate with optical equipment, it is necessary to take certain measures to enlarge the natural shapes and dimensions of the body cavities to provide the necessary overview and a greater freedom of movement. To achieve this, it is already known to enlarge organs or joints by means of gaseous or liquid media. This enlargement can be obtained only with a certain overpressure of the internal media in relation to the normal air pressure. The introduction of viewing or treatment instruments then brings about a pressure equalization, with the result that the original condition of overpressure cannot be maintained.

The object of the invention is to disclose a device for introducing viewing instruments (endoscopes) and/or surgical instruments, with which said instruments can be brought into various positions in the body cavities without an increased internal pressure in the body cavities being reduced.

The object of the invention is achieved by a device for introducing an endoscope or a surgical tool into body cavities with a feed for a flushing medium and an extractor for said flushing medium which includes a sluice, insertable into the body cavity from outside, with a cylindrical stem along whose inner wall extend two separate longitudinal grooves which at their ends comprise openings passing through the wall of the stem, the openings outside the body being connected to the feed and the extractor for the flushing medium, wherein an inserted cylindrical endoscope or tool tightly contacts with its outer wall the inner wall of the stem and thus together with the longitudinal grooves forms sealed channels for the flushing medium.

With this embodiment, the sluice, which is insertable into the body cavity, provides a seal with respect to the inserted viewing or treatment instrument, so that a possibly desired overpressure in the interior of the body cavity can be maintained. In addition, the exact guiding of the flushing medium, which may be gaseous or liquid, through the longitudinal grooves guarantees that the flushing medium enters the body cavity by a defined flow path from where it is again extracted in a defined manner. This guarantees efficient flushing of the viewing or operating area, as it is possible, through the feeding and dosed extracting of the flushing medium, to maintain the desired overpressure in the operating or viewing area. The viewing or treatment instrument can be longitudinally displaced and turned in the stem, so that the operating surgeon is able to position the instrument in the desired manner without being hindered by feed or extraction connections for the flushing medium. With conventional instruments, there are usually feed and extraction hoses on the instrument itself, so that, if the position of the instrument is changed, it is necessary also to move these hoses, which may hinder the operation.

A particular advantage of this arrangement is in the fact that the operating surgeon is able to bring the free end of the endoscope or the actual tool precisely into the area of the openings by pulling it back out of the stem, so that the inflowing flushing medium can directly clean the inlet window of the endoscope or the tool, should particles of tissue or similar material have collected there. This is made possible particularly by the fact that the inserted instrument itself forms part of the border of the flushing channels, so that, when the instrument is suitably pulled back, the flushing channels open toward the instrument.

A further advantage of the present device is to be seen in the fact that the part of the sluice which is insertable into the body, namely the stem, has an outside diameter which is only very slightly greater than the outside diameter of the instrument, so that the sluice part can readily be inserted into the desired position in the body without there being any major injury to the surrounding tissue.

The part of the stem outside the body may be provided with a seal which seals the stem from the endoscope or tool. This seal additionally safeguards the body cavity against pressure equalization with the environment. It is advantageous if the seal is in a sealing body mounted on the stem and is held in said sealing body by means of a union ring.

In a further preferred embodiment, the stem comprises an outward-pointing enlargement in the region of its free end. This enlargement has the advantage that, after the insertion of the sluice, the enlargement presses against the surrounding tissue, thus preventing unintentional withdrawl of the sluice. It is advantageous if the enlargement is on the side, facing away from the free end of the stem, of the openings disposed in the interior of the body. In this case the enlargement seals the body cavity at the point of insertion, thus additionally preventing pressure equalization between the body cavity and the environment. Furthermore, flushing medium issuing from the openings is prevented from escaping into the environment, i.e. this flushing medium is thereby introduced with precision into the body cavity.

It is particularly advantageous if the enlargement is in the form of a truncated cone and is tapered toward the free end of the stem. This facilitates the insertion of the sluice into the body cavity, while withdrawal is possible only through application of a controlled, greater force.

In a further preferred embodiment, the endoscope or the tool is surrounded by a cylindrical protective sleeve. This protective sleeve protects, for example, an optical fiber against damage due to kinking or damage by instruments used in the vicinity. It is advantageous if the protective sleeve is, at least on the outside, of electrically insulating design, since this prevents the possibility of damage to the instrument through electrocoagulation in the vicinity of the instrument. The protective sleeve, which is slipped over the endoscope or tool, may be releasably connected to the endoscope or tool.

In a preferred embodiment of the invention, the stem consists of an outer tube, which comprises the openings, and of an inner tube, said inner tube being inserted into said outer tube and having slots in its wall which are each aligned with two openings of the outer tube and form the longitudinal grooves. This results in the particularly simple manufacture of a stem which is provided with longitudinal grooves on the inside and which, in conjunction with the cylindrical instrument, forms sealed channels.

The following description of a preferred embodiment of the invention explains the invention in greater detail with reference to the drawings.

FIG. 1 shows a side view of a partially cut-away device for introducing an endoscope into the body;

FIG. 2 shows a top view of the device in FIG. 1; and

FIG. 3 shows a sectional view on line 3—3 in FIG. 1.

The device shown in the drawings comprises two parts, namely a sluice part 1 and an instrument 2, in the present case an endoscope for viewing an operating area.

The sluice part 1 comprises a cylindrical stem 3 which consists basically of an outer tube 4 and an inner tube 5 inserted into the latter, said inner tube 5 being in tight contact with the inner wall of the outer tube. Both tubes 4 and 5 are inserted by one end into a sealing body 6 and align with a hole 7 in the sealing body, the diameter of the sealing body corresponding to the inside width of the inner tube 5.

In the part of the tube 4 which is inserted into the sealing body 6, the outer tube 4 comprises two diametrically opposite openings 8 and 9 which are connected to radial channels 10 and 11, respectively, in the sealing body 6. The channels 10 and 11 are adjoined by connections 12 and 13, respectively, for a feed line and an extraction line (neither shown in the drawing), respectively, for a flushing medium. Disposed in the connections 12 and 13 are dosing valves which can be adjusted in the desired manner by means of rotary knobs 14 and 15, respectively.

Disposed in the outer tube 4 at the opposite end from the sealing body 6 are two further, diametrically opposite openings 16 and 17 which connect the interior of the outer tube 4 to the environment.

The inner tube 5 comprises two diametrically opposite slots 18 and 19 which are each aligned with openings 8 and 16, and 9 and 17, respectively, in the outer tube 4 and thus connect said openings to each other.

A tubular part 20 of the instrument 2 is insertable into the inner tube 5 of the stem 3. In the embodiment shown, this is a circularly cylindrical glass optical fiber 21 which is surrounded by a tubular protective sleeve 22. Said protective sleeve may consist of metal; it is also possible for the protective sleeve to be made of a sterilizable plastic. If metal is used, it is advantageous if the protective sleeve 22 has an electrically insulating outer layer, for example an oxide layer or a plastic coating.

Said protective sleeve 22 is slipped onto the glass optical fiber 21 and is fixed in its position on the instrument since the conical recess 24 of an end piece 23 is pressed by means of a compression spring 25 against a conical shoulder 26 of the endoscope surrounding the optical glass fiber. For this purpose, the compression spring 25 is supported, firstly, on the end piece and, secondly, on a union cover 27 which is screwed onto the inside thread 28 of a sleeve 29 surrounding the shoulder 26. The optical glass fiber, the shoulder 26 and the sleeve 29 are connected to a knob-shaped part 30 to which it is possible by way of a radially projecting nozzle 31 to connect a further light guide (not shown in the drawing) through which the light incident on the optical glass fiber 21 can be supplied to a known viewing apparatus, for example a television camera (not shown in the drawing).

The outside diameter of the protective sleeve 22 corresponds to the inside diameter of the inner tube 5, so that, when the tubular part 20 is inserted into the sluice part 1, the protective sleeve 22 sealingly contacts the inner wall of the inner tube 5 and, together with the slots 18 and 19 as well as the inner wall of the outer tube 4, forms two separate channels for the feeding and extraction of the flushing medium.

The part 20 is longer than the stem 3, so that the free end 32 of the part 20 projects out of the stem. This free end is, for example, the light inlet of the optical glass fiber; if using a machining tool instead of an optical glass fiber, the free end may bear, for example, a milling head which can be driven by a drive shaft disposed inside the protective sleeve 22.

Held in a step-wise enlarged hole 33 in the sealing body 6 is a sealing disc 34 which, with its inner edge, contacts the protective sleeve 22 of the tubular part 20. The sealing disc 34 is pressed against a step of the hole 33 by a union ring 36 by means of a spacer 35 and is thus held in this position.

The sluice part 1 is sealed with respect to the inserted tubular part 20 as a result of the tight contact of the tubular part 20 on the inner wall of the inner tube 5 and additionally by the sealing disc 34.

Directly next to the openings 16 and 17 at the free end of the stem 3, the outer tube 4 bears a truncated conical enlargement 37 which is tapered toward the free end of the stem, so that it does not hinder the insertion of the sluice part into the body, yet holds the sluice part in the body after insertion.

After the insertion of the sluice part into the body, the tubular part 20 of the instrument 2 can be inserted into the sluice part. The flushing medium is fed and extracted exclusively through the sluice part, i.e. the instrument itself is not required for this, with the result that the instrument can, without any hindrance, be turned or moved in the longitudinal direction in the sluice part. Because the sluice part is sealed with respect to the instrument, the increased internal pressure in the body can be maintained, even if the position of the instrument in the sluice part is altered. Once again without loss of pressure, it is possible to clean the inlet window of an endoscope or the tool of a machining instrument when cylindrical part 20 is withdrawn out of the sluice part to such an extent that the optical window or the tool comes into the region of the openings 16 and 17. The flushing medium thus flows directly past the window or the tool and cleans the latter. When the instrument is subsequently re-inserted into the sluice part, the flushing medium again escapes in the desired manner through the opening 16 into the environment and is again drawn in through the opening 17.

What is claimed is:

1. Device for introducing an endoscope or a surgical tool into body cavities, the device having a feed for a flushing medium and an extractor for said flushing medium, comprising:

a sluice, insertable into the body cavity from outside, with a cylindrical stem having a free end insertable into the body cavity, said stem comprising an outer tube and an inner tube inserted into said outer tube, said outer tube having openings through its wall at locations outside and inside the body cavity, and said inner tube having at its interior surface two separate longitudinal grooves which are each aligned with two of said openings of said outer tube, the openings outside the body being connected to the feed and the extractor for the flushing medium, and wherein an inserted cylindrical endoscope or tool tightly contacts with its outer wall the inner wall of the stem and thus together with the longitudinal grooves forms sealed channels for the flushing medium.

2. Device as defined in claim 1, wherein disposed on the part of the stem outside the body is a seal which seals the stem from the endoscope or the tool.

3. Device as defined in claim 2, wherein the seal is in a sealing body mounted on the stem and is held in said sealing body by means of a union ring.

4. Device as defined in claim 1, wherein the stem in the region of its free end comprises an outward-pointing enlargement.

5. Device as defined in claim 4, wherein the enlargement is on the side, facing away from the free end of the stem, of the openings disposed in the interior of the body.

6. Device as defined in claim 5, wherein the enlargement is in the form of a truncated cone and is tapered toward the free end of the stem.

7. Device as defined in claim 1, wherein the endoscope or tool is surrounded by a cylindrical protective sleeve.

8. Device as defined in claim 7, wherein the protective sleeve is, at least on the outside, of electrically insulating design.

9. Device as defined in claim 8, wherein the protective sleeve, which is slipped over the endoscope or tool, is releasably connected to the endoscope or tool.

* * * * *